United States Patent [19]
Fernandez

[11] Patent Number: 5,147,374
[45] Date of Patent: Sep. 15, 1992

[54] PROSTHETIC MESH PATCH FOR HERNIA REPAIR

[76] Inventor: Alfredo Fernandez, 16145 Carden Dr., Odessa, Fla. 33556

[21] Appl. No.: 802,504

[22] Filed: Dec. 5, 1991

[51] Int. Cl.⁵ .............................................. A61B 17/00
[52] U.S. Cl. .................................... 606/151; 623/12; 66/169 R
[58] Field of Search ..................... 606/151; 623/11, 12; 66/190, 193, 194, 195, 169 R

[56] References Cited

U.S. PATENT DOCUMENTS

| | | | |
|---|---|---|---|
| 2,671,444 | 3/1954 | Pease | 606/151 |
| 3,272,204 | 9/1966 | Artadi et al. | 606/151 |
| 4,347,847 | 9/1982 | Usher | 606/151 |
| 4,769,038 | 9/1988 | Bendavid et al. | 623/13 |
| 4,781,191 | 11/1988 | Thompson | 606/151 |

OTHER PUBLICATIONS

Ethicon's Brochure "Enopath'es Endoscopic" USA, 1987.
Schultz er al; Laser Laparoscopic Herniorraphy? A Clinical Trail Preliminary Results; Journal of Lararuendoscopic Surgery; vol. 1, No. 1990.
Spaw et al; Laparoscopic Hernia Repair; The Anatomic Basis Journal of Lapoendoscopic Surgery, vol. 1, No. 5, 1991.
Ger, The Laparoscopic Management of Groin Hernias; Contemporary Surgery, Oct. 1991 vol. 39, No. 4.

*Primary Examiner*—Stephen C. Pellegrino
*Assistant Examiner*—Gary Jackson
*Attorney, Agent, or Firm*—Herbert W. Larson

[57] ABSTRACT

A patch is made from a rolled up first flat sheet of polypropylene or polytetrafluroethylene surgical mesh. One end of the rolled up mesh has multiple slits to provide multiple flared out flaps stitched to a second flat sheet of surgical mesh. The patch is compressed into a longitudinal cylindrical structure and is inserted through a trocar into an opening of a hernia. The rolled up first flat sheet is inserted through the opening and the flaps and second flat sheet are stapled to the patient's tissue adjacent the opening.

12 Claims, 4 Drawing Sheets

PROSTHETIC MESH PATCH FOR HERNIA REPAIR

BACKGROUND OF THE INVENTION

1. Field of The Invention

This invention relates to laparoscopic hernia repair. More particularly, it refers to the use of a flared mesh patch to repair an inguinal hernia during laparoscopic procedures.

2. Description of The Prior Art

The traditional inguinal approach to hernia repair results in recurrence ranging from seven to twenty-one percent for primary repair and up to eighteen percent after repair of recurrent hernias. In addition, recovery periods associated with herniorrhaphy can be lengthy and painful, sometimes lasting from three to six weeks. See the Journal of Laparoendoscopic Surgery, Volume 1, No. 5, p. 269, 1991, Mary Ann Liebert, Inc., publishers. In seeking to improve on these results and reduce recovery periods associated with herniorrhaphy, surgeons have been carrying out laparoscopic hernia repair employing laser surgery techniques. See the Journal of Laparoendoscopic Surgery, Vol. 1, No. 1, 1990, pages 41–45; and Contemporary Surgery, October 1991, Vol. 39, No. 14, pages 15–19.

While it appears that laparoscopic hernia repair techniques have been successful, the insertion of polypropylene mesh into the opening in the inguinal region causing the hernia has sometimes resulted in bulging of the inguinal region. This could be caused by movement of the rolled up surgical mesh inserted into the hernia opening. A more perfect prosthetic mesh patch that can be delivered to the hernia site by laparoscopic techniques is needed to reduce side effects and recurrences from laparoscopic hernia repair surgery.

SUMMARY OF THE INVENTION

I have developed an improved patch for use in laparoscopic hernia repair surgery.

My patch is made by rolling up a first sheet of a surgical plastic mesh, maintaining the rolled up configuration by at least two circumferential bands of cat gut, cutting longitudinal slits in one end of the rolled up mesh and flaring out the multiple flaps formed by the slits. A second planar sheet of surgical plastic mesh is then stitched to the flared out flaps. The flaps and planar sheet are then compressed together as a longitudinal extension of the first rolled up sheet and inserted into a cylindrical plastic delivery tube. The tube is inserted into the abdomen via a trocar and the patch is pushed out by a plunger into the hernia opening. The second planar sheet is stapled to the tissue adjacent the hernia opening with a stapling gun.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1A:
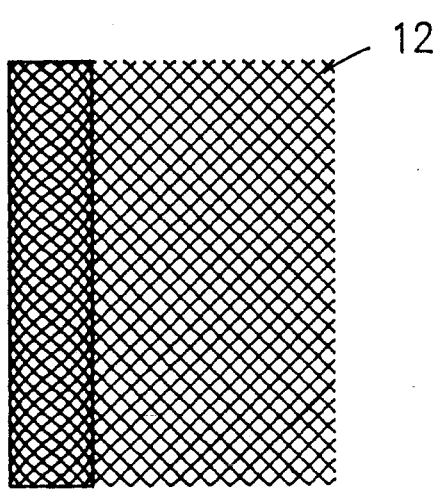
FIG. 1A is a top plan view of a piece of surgical plastic mesh being rolled into a cylindrical shape.
Figure 1B:
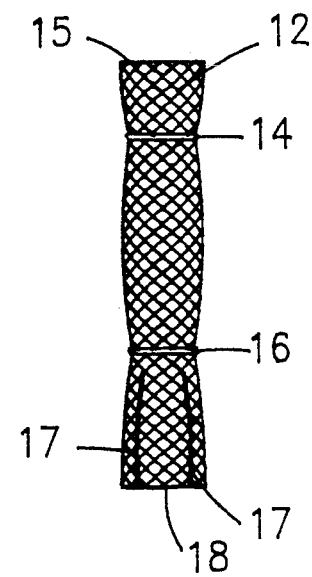
FIG. 1B is an elevation view of the rolled up surgical mesh of FIG. 1A with slits at one end.

Throughout the following detailed description, the same reference numerals refer to the same elements in all figures.

Figure 2:
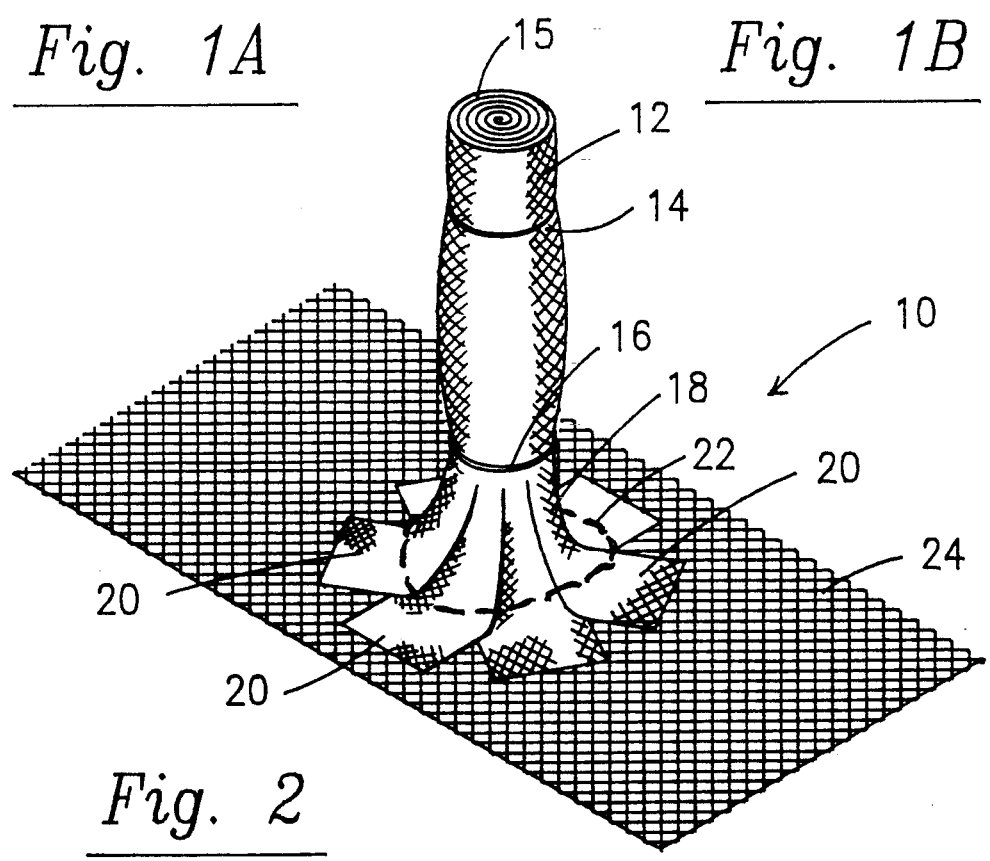
FIG. 2 is a perspective view of the patch of this invention.
Figure 3:
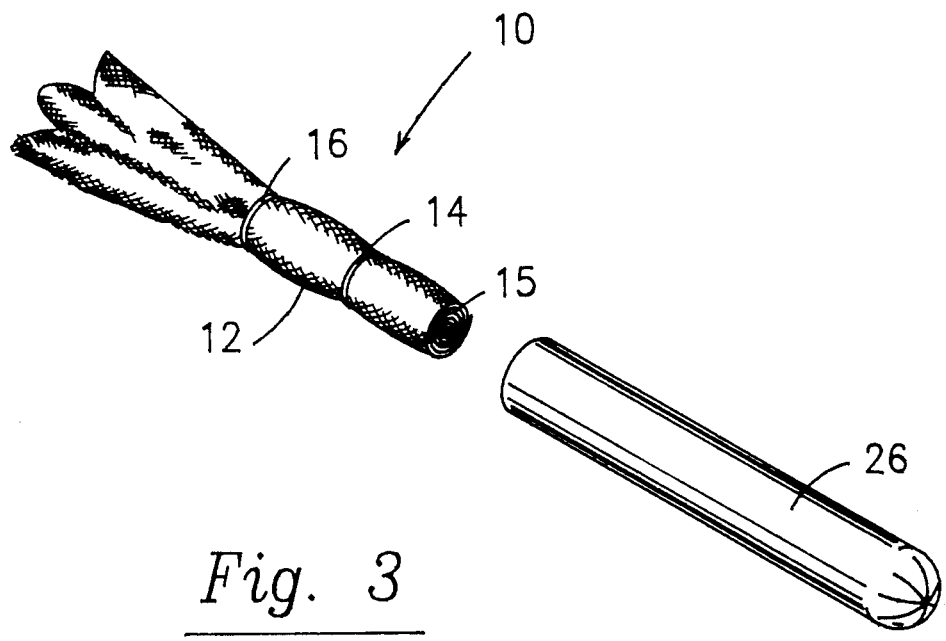
FIG. 3 is a perspective view of a rolled up patch being inserted into a delivery tube.
Figure 4:
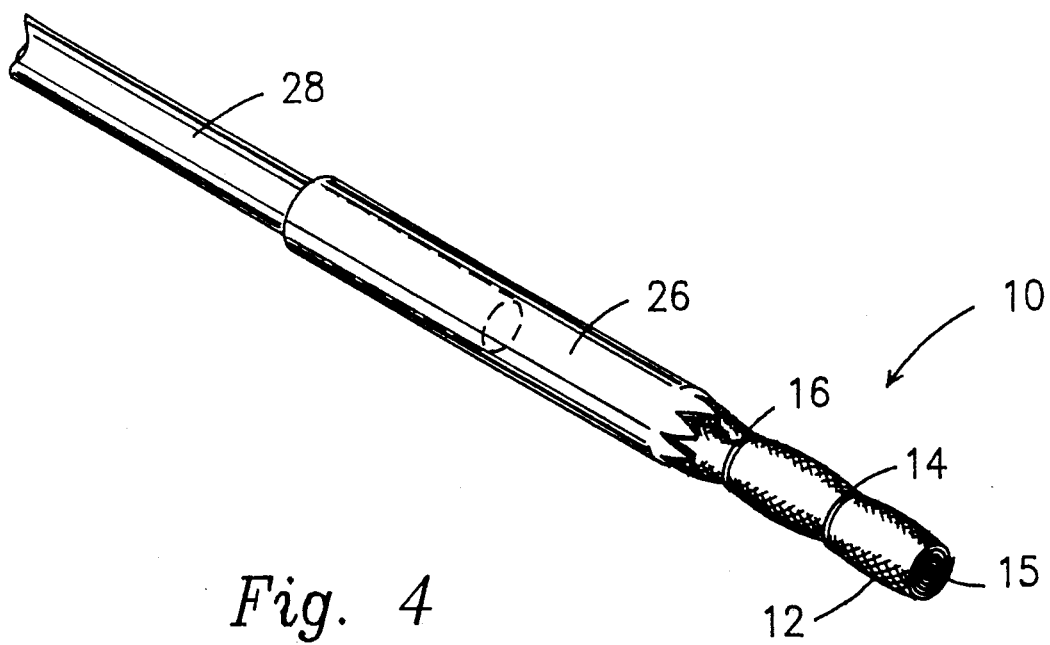
FIG. 4 is a perspective view partially in phantom showing the patch being pushed out of the delivery tube.
Figure 5:
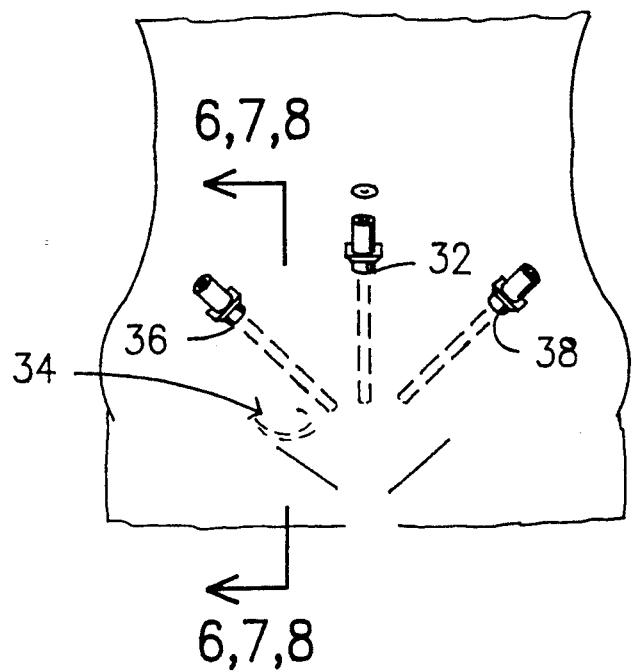
FIG. 5 is a frontal view of a patient undergoing laparoscopic hernia repair surgery.
Figure 6:
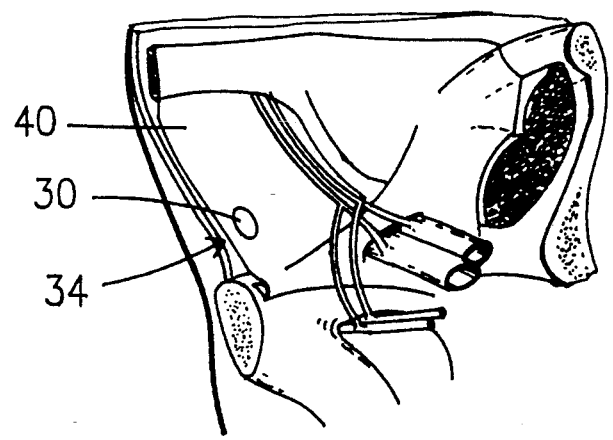
FIG. 6 is a section view along lines 6—6 of FIG. 5 through the abdomen of a patient with a hernia visible.
Figure 7:
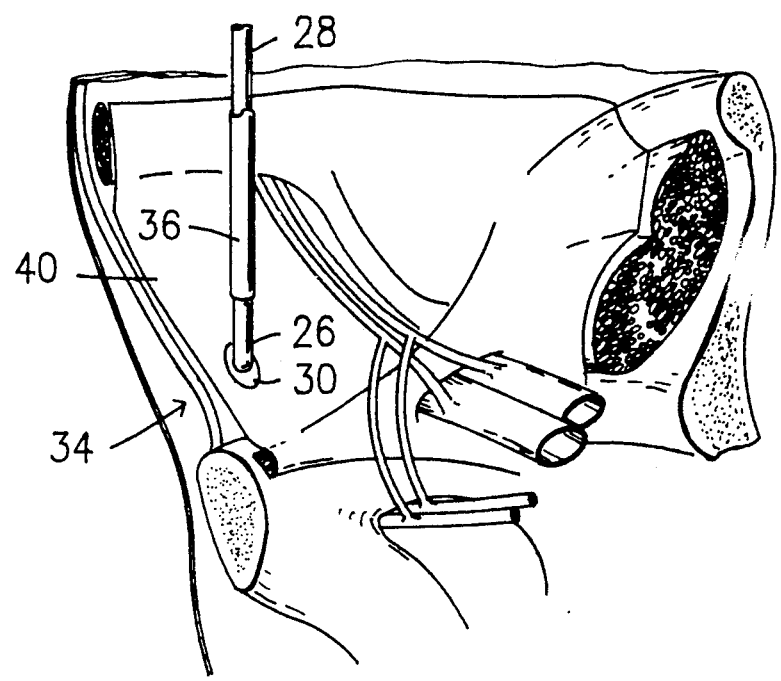
FIG. 7 is a section view along lines 6—6 of FIG. 5 adding a showing of the patch being inserted into the opening of the hernia.
Figure 8:
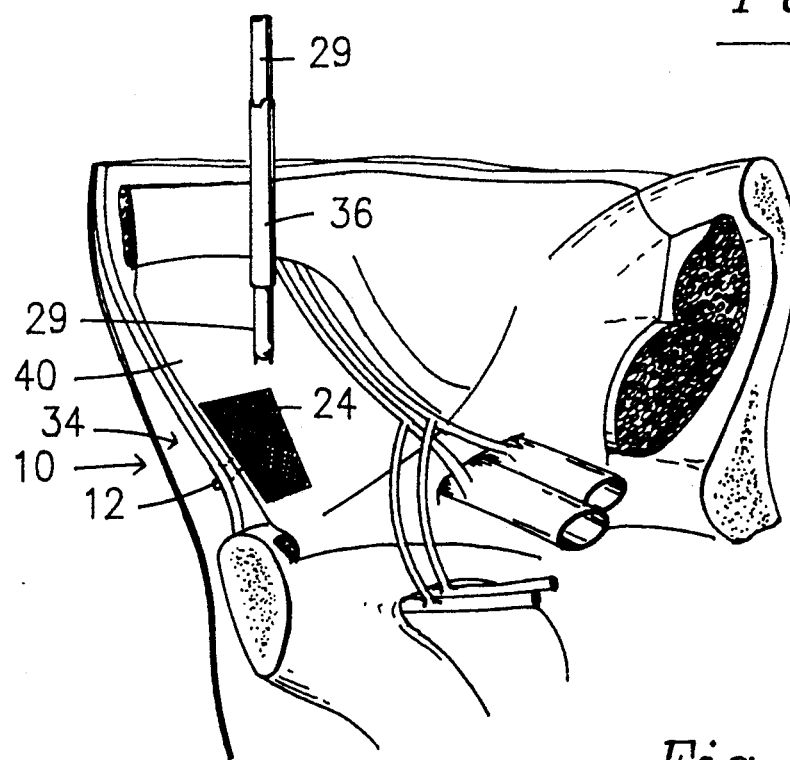
FIG. 8 is a section view along lines 6—6 of FIG. 5 adding a showing of the patch in place over the opening of the hernia.

The prosthetic mesh patch 10 of the invention shown in FIG. 2 has a first rolled up surgical plastic mesh portion 12 tied together by cat gut 14 near a first end 15 and a cat gut 16 about midway to two-thirds down the rolled up surgical plastic mesh 12. Approximately five scissor slits 17 are made in the second end 18 of the rolled surgical plastic 12 so that six flared flaps 20 are produced. The flaps 20 are stitched 22 to a flat sheet 24 of surgical mesh. Thereafter, the patch 10 is rolled up as shown in FIG. 3 and inserted into a plastic carrier 26. An elongated plunger 28 as shown in FIG. 4 is used to push out the patch 10 from its carrier 26 into the opening 30 of the hernia.

The patch 10 is used for repeating inguinal hernias. In repairing such a hernia, a patient is brought into an operating room and placed in the supine position. General endotracheal anesthesia is induced and the abdomen, groin and genitalia are prepped and draped in a sterile fashion using betadine solution. The patient is placed in a Trendelenburg position. A small vertical incision is made in the lower edge of the umbilicus and a Verres needle is inserted into the abdomen and a pneumoperitoneum of approximately three liters is carried out. A ten millimeter trocar 32 is then placed through the umbilicus and a laparoscope is threaded through the trocar 32. The abdomen is inspected and the repair site 34 is visually observed. Usually there is a small sac associated with the hernia opening. A five millimeter trocar 36 is then inserted in the right abdomen and a twelve millimeter trocar 38 in the left abdomen parallel with the umbilicus. The dissecting trocars are inserted into the abdomen and the hernia sac is dissected out using a contact YAG laser to excise the sac. Normally, no bleeding is encountered. The patch 10 is backloaded into a twelve millimeter sleeve of an endopath stapler 29 and inserted into the abdomen through trocar 36. Alternatively, the patch is pushed out of carrier 26 by plunger 28 through the trocar 36. The patch 10 is inserted into the opening 30 so that the rolled up portion 12 is completely inserted into the opening. The flared portion 20 with the second plastic mesh sheet 24 is then stapled in place to adjacent tissue by the endopath stapler 29. The incisions are repaired and the patient is then sent for recovery.

The stapler 29 used for stapling the patch to the adjacent tissue is an endoscopic tissue repair stapling gun, such as, the ENDOPATH ES Endoscope sold by Ethicon, Inc., a division of Johnson & Johnson Co. Such a stapler is designed for use with a twelve millimeter disposable surgical trocar.

The surgical plastic mesh employed to make the patch of this invention can be any of the surgical plastic meshes suitable for use in hernia operations, such as, PROLENE, sold by Ethicon, Inc. Generally, the plastic mesh is either a polypropylene or a polytetrafluoroethylene. The stitches 22 used to keep the second plastic mesh 24 in place over the flaps 20 are also either a polypropylene or polytetrafluoroethylene thread commonly used in surgical sutures. The size of the plastic surgical mesh used in this invention is usually a two and one-half by four inch sheet of expanded polytetrafluoroethylene or polypropylene and such a sheet can be used for either the first rolled up mesh 12 or the second flat mesh 24. The mesh 24 has to be large enough to overlap the opening of the hernia and previde adequate room for stapling into the adjacent peritoneum 40.

Modification of the materials used in the patch of this invention can be made depending upon the availability of new types of surgical mesh and improvements in the stitching or stapling materials.

Having thus described the invention, what is claimed and desired to be secured by Letters Patent is:

1. A surgical flared patch for use in laparoscopic hernia repair comprising
   a rolled up sheet of a surgical plastic mesh maintained in a rolled up form by at least two bands and multiple longitudinal cuts in a first end of the rolled up mesh to form multiple flared out flaps,
   a planer sheet of a surgical plastic mesh permanently attached to the flaps in a flared out position, the flaps and planer sheet being capable of compressing together as a longitudinal extension of the rolled up sheet of surgical plastic mesh and inserted into a cylindrical plastic delivery tube.

2. The surgical flared patch according to claim 1 wherein the rolled up sheet and planar sheet of surgical plastic mesh is polytetrafluoroethylene.

3. The surgical flared patch according to claim 1 wherein the rolled up sheet and planar sheet of surgical plastic mesh is polypropylene.

4. The surgical flared patch according to claim 1 wherein the planar sheet of surgical plastic mesh is stitched to the flaps by a plastic suture thread.

5. The surgical flared patch according to claim 4 wherein the plastic suture thread is polytetrafluoroethylene.

6. The surgical flared patch according to claim 4 wherein the plastic suture thread is polypropylene.

7. The surgical flared patch according to claim 1 wherein the bands maintaining the rolled up surgical plastic mesh are cat gut.

8. The surgical flared patch according to claim 1 wherein five longitudinal slits are made in a first end of the rolled up mesh to form five flared out flaps.

9. In a method of repairing an inguinal hernia using laparoscopic surgical procedures wherein an incision is made in a patient's umbilicus and in the right lower abdomen and in the left lower abdomen and a patch is delivered via a trocar to an opening to be repaired, the improvement wherein,
   the patch inserted into the opening is a rolled up sheet of a surgical plastic mesh maintained in a rolled up form by attaching at least two bands around the rolled up mesh and then making multiple longitudinal cuts in a first end of the rolled up mesh to form multiple flared out flaps, the flaps then being stitched to a planar sheet of plastic surgical mesh, the patch then inserted into the opening by a second end of the rolled up sheet of surgical plastic so that the rolled up portion of the patch enters the opening and the flaps and planar sheet of plastic surgical mesh are displayed out over an entrance to the opening, and then the planar sheet of plastic surgical mesh is stapled to adjacent tissue to retain the patch in position.

10. The method according to claim 9 wherein the surgical mesh employed is polypropylene.

11. The method according to claim 9 wherein the surgical mesh employed is polytetrafluoroethylene.

12. The method according to claim 7 wherein the patch is compressed into a cylindrical tube for delivery to the hernia site.

* * * * *